(12) United States Patent
Wiss et al.

(10) Patent No.: US 9,156,761 B2
(45) Date of Patent: Oct. 13, 2015

(54) PROCESS FOR PREPARING POLYETHER POLYOLS

(71) Applicant: BASF SE, Ludwigshafen (DE)

(72) Inventors: Kerstin Wiss, Mannheim (DE); Sirus Zarbakhsh, Hong Kong Pok Fu Lam (CN); Achim Loeffler, Speyer (DE); Peter Deglmann, Mannheim (DE); Michael Limbach, Worms (DE); Ronald Lindner, Dossenheim (DE); Severine Lavy, Heidelberg (DE); Michael Ludwik Lejkowski, Mannheim (DE)

(73) Assignee: BASF SE, Ludwigshafen (DE)

( * ) Notice: Subject to any disclaimer, the term of this patent is extended or adjusted under 35 U.S.C. 154(b) by 198 days.

(21) Appl. No.: 13/850,578

(22) Filed: Mar. 26, 2013

(65) Prior Publication Data

US 2013/0274526 A1    Oct. 17, 2013

Related U.S. Application Data

(60) Provisional application No. 61/615,381, filed on Mar. 26, 2012.

(51) Int. Cl.
*C08G 65/00* (2006.01)
*C07C 41/03* (2006.01)

(52) U.S. Cl.
CPC ..................................... *C07C 41/03* (2013.01)

(58) Field of Classification Search
CPC ................................ C07C 41/03; C07C 41/11
USPC ........... 528/405, 408; 564/565; 568/623, 624, 568/620, 679
See application file for complete search history.

(56) References Cited

U.S. PATENT DOCUMENTS

| 2010/0029961 A1* | 2/2010 | Triller et al. .................. 549/539 |
| 2010/0261870 A1* | 10/2010 | Loeffler et al. ............... 528/425 |
| 2011/0144296 A1* | 6/2011 | Li et al. ........................... 528/27 |

FOREIGN PATENT DOCUMENTS

| WO | WO 2009/013344 A1 | 1/2009 | |
| WO | WO 2009013344 | * 1/2009 | .............. B01J 31/02 |
| WO | WO 2011/141492 A1 | 11/2011 | |

* cited by examiner

*Primary Examiner* — Shane Fang
(74) *Attorney, Agent, or Firm* — Oblon, McClelland, Maier & Neustadt, L.L.P.

(57) ABSTRACT

The present invention relates to a process for preparing polyetherols by catalytic ring-opening polymerization, wherein at least one nitrogen-containing cyclic precatalyst compound is used.

17 Claims, 1 Drawing Sheet

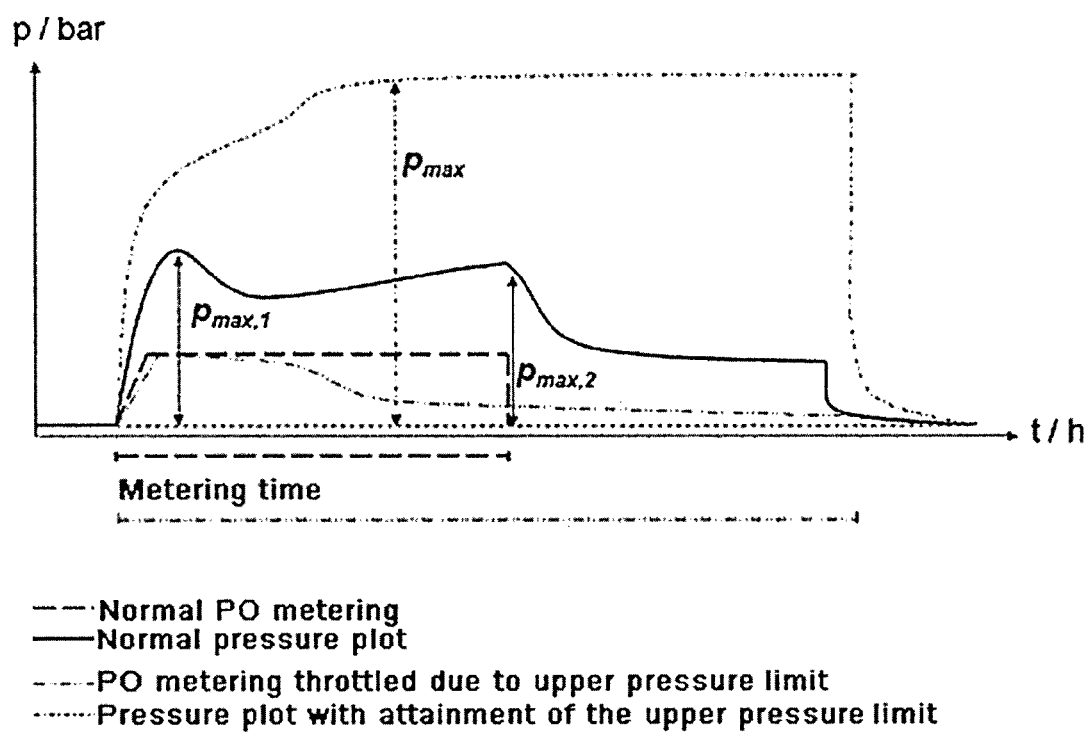
— — Normal PO metering
——— Normal pressure plot
— - — PO metering throttled due to upper pressure limit
······ Pressure plot with attainment of the upper pressure limit

PROCESS FOR PREPARING POLYETHER POLYOLS

CROSS REFERENCE TO RELATED APPLICATION

This application claims priority to U.S. Provisional Patent Application No. 61/615,381, filed on Mar. 26, 2012, herein incorporated in its entirety by reference.

The present invention relates to a process for preparing polyether polyols (also called polyetherols) by catalytic ring-opening polymerization, wherein at least one nitrogen-containing cyclic precatalyst compound is used.

N-Heterocyclic carbenes (NHCs) have been known for some years as initiators or organocatalysts for ring-opening polymerization (Dove et al., Polymer 47 (2006), 4018). Application to the catalytic polymerization of ethylene oxide (EO) was first described in 2006 (ACS Polymer Preprints, 47 (2006), 99). Recently, Raynaud et al. (JACS, 131 (2009), 3201; WO2009/013344 in cooperation with Rhodia) also described the stoichiometric ring opening of ethylene oxide (EO) in solution, which forms zwitterionic PEG (polyethylene glycol) oligomers after long reaction times. The patent claims all industrially relevant alkylene oxides as monomers and all standard carbene structures as catalysts, but examples are given only for EO (and thus possible advantages of the NHC catalysts for propylene oxide (PO) are not mentioned). Finally, the same research group in 2010 also published a paper regarding PO polymerization with monofunctional starters under similar reaction conditions (Chem. Commun., 46 (2010), 3203), but no advantages are evident apart from the freedom of the reaction from metal. None of these studies claim use for the preparation of polyurethane (PU) or describe it as particularly advantageous.

Patent application WO 2011/141492 describes the ring-opening polymerization of alkylene oxides with NHC catalysts for preparation of polyether- and polyesterols. The advantages mentioned for this invention are particularly the high degrees of polymerization with PO (>5 PO per OH group of the starter, in contrast to conventional organocatalysts) and the possibility of EO end-capping of PPG (polypropylene glycol) cores. Conventional catalysts either lead to a considerable level of monofunctional by-products (KOH catalysis) or do not allow a well-defined end cap on the majority of the secondary hydroxyl groups (in the case of double metal cyanide (DMC) catalysis).

Typical organocatalyses with NHCs are based on the nucleophilicity or basicity thereof. However, precisely these properties constitute a crucial barrier to the use of NHCs: free NHCs are typically hydrolysis- and oxidation-sensitive (J. Organomet. Chem., 617 (2001), 242). One option in the process is therefore to release the active NHC species from precatalysts in situ.

One possibility for this purpose is the use of adducts of the NHCs, for example with alcohols, chloroform, $CS_2$, $CO_2$:

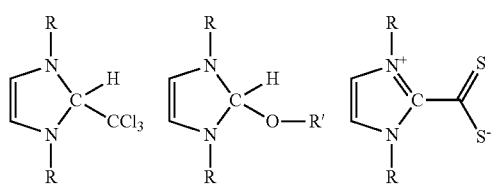

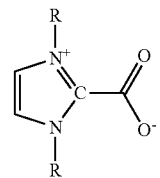

The latter adducts are referred to hereinafter as imidazolium carboxylates.

The N,N'-dialkylimidazolium carboxylates described above by way of example are an interesting class of precatalysts, because $CO_2$ as a by-product of the decomposition is not disruptive in the catalysis; it may be incorporated by reaction, but can in any case remain in the product.

The release of NHC from these precatalysts is, however, only minor at room temperature, and increases significantly in glycol only above 140° C. (in the case of dimethylimidazolium carboxylate), as shown by thermogravimetric studies (Eur. J. Inorg. Chem., 2009, 1681; Tetrahedron Lett., 46 (2005), 2141).

Since the release of NHC from these precatalysts usually takes place only at high temperatures, judging by the prior art, a large amount of energy has to be supplied. However, the high temperatures are problematic for the subsequent reaction of alkylene oxides with initiators, for example alcohols, since side reactions then occur to an increased extent; some starter compounds also do not withstand relatively high temperatures for long periods and decompose.

By increasing the temperature, the equilibrium between $CO_2$ adduct and the catalytically active species (NHC adduct) can thus be shifted in the desired direction. However, it is to be expected that the equilibrium will shift again in the direction of the $CO_2$ adduct as soon as the temperature is lowered again, since $CO_2$ is not removed from the equilibrium (prior to reaction with alkylene oxides).

It was thus an object of the present invention to provide a process for preparing polyetherols which allows efficient release of the catalytically active species without any unwanted side reactions during the reaction phase with alkylene oxides.

This object is surprisingly achieved by the process described in the claims.

It has namely been found that, even after a brief temperature increase, the catalytically active species, even when temperatures have subsequently been lowered again, is surprisingly available for the reaction with alkylene oxides; the equilibrium thus does not shift, as would be expected, when the temperature is reduced, back in the direction of the $CO_2$ adduct, which is possibly attributable to an interaction with the starter.

The present application therefore provides a process for preparing polyetherols by catalytic ring-opening polymerization of at least one alkylene oxide with at least one Zerevitinov-active compound Z1 and optionally at least one Zerevitinov-active compound Z2, wherein, in a step (i), at least one nitrogen-containing cyclic compound (A) selected from the group consisting of compounds with the formula (I)

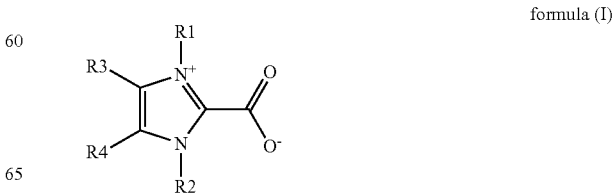

where R1 and R2 are each independently selected from alkyl and aryl, R3 and R4 are each independently selected from H, alkyl, aryl, or where R1 and R3, R3 and R4 or R2 and R4 form a ring, is initially charged together with at least one Zerevitinov-active compound Z1 or a mixture thereof, and heated to a temperature in the range from 140° C. to 180° C., preferably 150° C. to 170° C., for a duration of 5 to 30 minutes, preferably 10 to 25 minutes, and, in a step (ii), the metered addition of the at least one alkylene oxide is conducted, optionally in the presence of Z2.

BRIEF DESCRIPTION OF THE DRAWING

FIG. 1 shows a schematic diagram of the time course experiment of metering profiles.

In the context of the present application, "polyetherols" mean a compound having more than one OH group, preferably more than two OH groups.

A "Zerevitinov-active compound" relates to compounds which are acidic enough to protonate standard Grignard compounds to give the hydrocarbon. Examples of "Zerevitinov-active compounds" are alcohols and amines.

Some of the compounds (A) are commercially available, for example from Sigma Aldrich. The preparation of the compounds (A) has been described many times in the literature, for example in Schossler, W.; Regitz, M. Chem. Ber. 1974, 107, 1931, and Kuhn, N.; Steimann, M.; Weyers, G. Z. Naturforsch. 1999, 54b, 427, and Holbrey, J. D.; Reichert, W. M.; Tkatchenko, I.; Bouajila, E.; Walter, O.; Tommasi, I.; Rogers, R. D. Chem. Commun. 2003, 28, and in Duong, H. A.; Tekavec, T. N.; Arif, A. M.; Louie, J. Chem. Commun. 2004, 112.

In one embodiment of the invention, R1 and R2 in formula (I) are each primary alkyl groups.

In a further embodiment of the invention, R1 in formula (I) is a primary and R2 a secondary alkyl group.

In a further embodiment of the invention, R1 and R2 in formula (I) are each secondary alkyl groups.

Preferably in accordance with the invention, step (ii) is not conducted until after the end of step (i); however, step (ii) can also already commence during step (i).

In a preferred embodiment of the process according to the invention, the temperature during the reaction with the at least one alkylene oxide in step (ii), after the end of step (i), is in the range from 90° C. to 140° C., preferably in the range from 100° C. to 130° C.

The alkylene oxides for the process according to the invention are preferably selected from the group comprising:

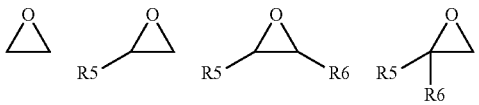

where: R5 and R6 are each selected from the group comprising alkyl, aryl, alkenyl.

Alkyl here is preferably a radical selected from the group of the C1- to C10-alkyl compounds, preferably C1 to C2 compounds, more preferably C1 compounds.

Aryl is preferably a phenyl radical.

Alkenyl is preferably a radical selected from the group of C2- to C10-alkenyl compounds, preferably a C3-alkenyl compound.

In a preferred embodiment of the invention, the alkylene oxide is selected from the group comprising ethylene oxide (EO), propylene oxide (PO) and butylene oxide. In a particularly preferred embodiment of the invention, mixtures comprising propylene oxide are used.

In one embodiment of the process according to the invention, the monomers M or content thereof are varied during the reaction. Therefore, the process according to the invention also allows the application of an ethylene oxide (EO) end cap.

Copolymerization, for example with lactones, lactide and/or cyclic siloxanes, is also possible by the process according to the invention.

Examples of suitable lactones for the copolymerization with alkylene oxides are substituted or unsubstituted lactones with 4-membered or larger rings, for example β-propiolactone, δ-valerolactone, ε-caprolactone, methyl-ε-caprolactone, β,β-dimethyl-β-propiolactone, β-methyl-β-propiolactone, α-methyl-β-propiolactone, α,α-bis(chloromethyl) propiolactone, methoxy-ε-caprolactone, ethoxy-ε-caprolactone, cyclohexyl-ε-caprolactone, phenyl-ε-caprolactone, benzyl-ε-caprolactone, ζ-enantholactone, η-caprylolactone, α,β,γ-trimethoxy-δ-valerolactone, or β-butyrolactone, and mixtures thereof. In one embodiment, ε-caprolactone is used.

The at least one Zerevitinov-active compound Z1 is preferably selected from the group consisting of alcohols, more preferably from the group of the polyols, especially glycerol, ethylene glycol, diethylene glycol, propylene glycol, dipropylene glycol, pentaerythritol, sorbitol, sucrose, C1- to C18-diols, castor oil, epoxidized and ring-opened fatty acids and esters thereof, trimethylolpropane, pentaerythritol, sugar compounds, for example glucose, sorbitol, mannitol and sucrose, polyhydric phenols, resols, for example oligomeric condensation products formed from phenol and formaldehyde and Mannich condensates formed from phenols, formaldehyde, dialkanolamines, and mixtures of at least two of the compounds listed.

Likewise preferably, at least one Zerevitinov-active compound Z1 is selected from the group consisting of amines, especially primary and secondary aliphatic and aromatic amines or mixtures thereof, most preferably selected from the group comprising hexamethylenediamine, ethylenediamine, propylenediamine, ethanolamine, orthocyclohexanediamine, aminocyclohexanealkylamine, and aromatic amines selected from the group comprising toluenediamine (TDA), especially 2,3 and 3,4 isomers of TDA, and diphenylmethanediamine (MDA) and polymeric MDA (p-MDA), melamine, and mixtures thereof.

The Zerevitinov-active compound Z1 may also comprise a plurality of amino groups and/or other Zerevitinov-active groups, for example OH groups.

In a further embodiment of the process according to the invention, at least two Zerevitinov-active compounds Z1 are used, at least one Zerevitinov-active compound Z1a being selected from the group consisting of alcohols, preferably from the above-specified group, and at least one Zerevitinov-active compound Z1b being selected from the group consisting of amines, preferably from the above-specified group.

The Zerevitinov-active compound Z2 is, in a preferred embodiment of the process according to the invention, selected from the group consisting of alcohols, more preferably selected from the group of alcohols specified for Z1.

The Zerevitinov-active compound Z2 is, in a further preferred embodiment of the process according to the invention, selected from the group consisting of amines, more preferably selected from the group of amines specified for Z1.

In one embodiment of the process according to the invention, the at least one Zerevitinov-active compound Z1 is the same as the at least one Zerevitinov-active compound Z2. In another embodiment of the process according to the invention, the at least one Zerevitinov-active compound Z1 does not correspond to the at least one Zerevitinov-active compound Z2.

In one embodiment of the process according to the invention, at least one compound Z1 is thus used in step (i) and then the alkoxylation is likewise conducted with Z1. In another embodiment of the process according to the invention, a compound Z1 is first used in step (i), but then the alkoxylation is conducted with a mixture of Z1 and a further compound Z2.

In a preferred embodiment of the process according to the invention, a vacuum is applied in step (i).

The present invention further provides a polyetherol preparable by the process according to the invention, and for the use of a polyetherol preparable by the process according to the invention for preparation of polyurethanes.

EXAMPLES

To illustrate some aspects of the present invention, some examples are given hereinafter. These are in no way intended to restrict the scope of the invention.

In the experiments, the starters (alcohols) and the catalyst were first initially charged in an autoclave, which was filled with nitrogen for inertization, then heated to 110-130° C. and degassed under reduced pressure for several hours. In the experiments with a thermal activation stage (i), the vessel was then heated to 160° C. for 20 minutes. After cooling to the desired reaction temperature, in both cases, the propylene oxide was then metered in continuously while stirring (stirrer speed 600 l/min) in step (ii). On completion of metered addition and reaction of the monomer, the vessel was then evacuated under reduced pressure for 30 minutes and then cooled to 25° C.

The schematic diagram of the course of the experiment shows the metering profiles (see legend: "PO metering . . . ") and the resulting pressure plots. Through the pressure plot, a statement is possible about the reactivity of the catalyst: At high reactivity, the propylene oxide was converted rapidly and no high pressure built up in the vessel. At lower reactivity, the propylene oxide accumulated and higher pressures were observed. On attainment of an upper pressure limit resulting from the design of the autoclave, it was necessary in some cases to deviate from a constant metering rate and to throttle or even to stop the metered addition (thinner broken lines in the schematic diagram), which led to an extension of the metering time and hence a reduction in the metering rate. In order to be able to quantify the pressure plot and compare the reactivity, the maximum pressures attained in the vessel, and also metering times and resulting mean metering rates, are reported hereinafter.

Example 1

A 300 ml vessel was initially charged with 20.0 g of glycerol, 7.69 g of diethylene glycol and 0.39 g of 1,3-dimethylimidazolium carboxylate. After the inertization, 149.63 g of propylene oxide were metered in at a reaction temperature of 115° C. In the course of this, the upper pressure limit of 9.79 bar was attained and therefore the metered addition was slowed. After a reaction completion time of 5 hours, 154 g of product were obtained.

OHN: 271 mg KOH/g
Viscosity: 228 mPas
$p_{max}$=9.79 bar
Metering time: 287 minutes
Metering rate: 0.52 g/min Example 2a A 300 ml vessel was initially charged with 20.0 g of glycerol, 7.69 g of diethylene glycol and 0.39 g of 1,3-dimethylimidazolium carboxylate. After the inertization and a thermal activation at 160° C., the vessel was cooled to the reaction temperature of 115° C. and then 149.63 g of propylene oxide were metered in. After a reaction completion time of 5 hours, 166.7 g of product were obtained.

OHN: 255 mg KOH/g
Polydispersity (GPC): 1.118
Viscosity: 178 mPas
$p_{max,1}$=3.54 bar
$p_{max,2}$=3.16 bar
Metering time: 226 minutes
Metering rate: 0.66 g/min Examples 2b-e Under analogous conditions to those described in example 2a, it was also possible to obtain a similar product with other catalysts. These catalysts differ only with regard to the 1,3-alkyl substitution (R1 and R2 in formula (I)) from the catalyst from example 2a. The respective substituents and the corresponding results are compiled in the table below.

| * | #2b | #2c | #2d | #2e |
|---|---|---|---|---|
| R1 | methyl | ethyl | n-propyl | isopropyl |
| R2 | ethyl | ethyl | n-propyl | isopropyl |
| m(cat.) | 0.42 g | 0.47 g | 0.55 g | 0.55 g |
| Activ. | yes | yes | yes | yes |
| Product | 168.4 g | 166.9 g | 165.2 g | 166.1 g |
| OHN | 258 | 254 | 257 | 259 |
| PDI | 1.120 | 1.111 | 1.108 | 1.113 |
| Visco | 187 | 177 | 181 | 192 |
| $p_{max,1}$ | 3.3 | 3.6 | 3.4 | 3.8 |
| $p_{max,2}$ | 3.1 | 3.2 | 3.3 | 3.5 |
| Time | 226 | 226 | 226 | 226 |
| Rate | 0.66 | 0.66 | 0.66 | 0.66 |

* Explanations: m(cat.) = mass of the catalyst, Activ. = activation at 160° C. for 20 minutes, OHN in mg KOH/g, PDI = polydispersity (GPC), Visco = viscosity in mPas, $p_{max,1\ and\ 2}$ in bar, Time = metering time in minutes, Rate = metering rate in g/min Example 3

A 300 ml vessel was initially charged with 20.0 g of glycerol, 7.69 g of diethylene glycol and 0.89 g of 1,3-dimethylimidazolium carboxylate. After the inertization and an activation at 160° C., a reaction temperature of 160° C. was maintained and then 149.63 g of propylene oxide were metered in. After a reaction completion time of 5 hours, 167.4 g of product were obtained.

OHN: 277 mg KOH/g
Polydispersity (GPC): 1.159
Viscosity: 142 mPas
$p_{max,1}$=4.06 bar
$p_{max,2}$=5.38 bar
Metering time: 240 minutes
Metering rate: 0.62 g/min Example 4

A 300 ml vessel was initially charged with 20.0 g of glycerol, 7.69 g of diethylene glycol and 0.89 g of 1,3-dimethylimidazolium carboxylate. After the inertization and an activation at 160° C., the vessel was cooled to a reaction temperature of 115° C. and then 149.63 g of propylene oxide were metered in. After a reaction completion time of 5 hours, 163.2 g of product were obtained, and it was found here, on evaluation of the pressure curve with regard to the decline in pressure during the reaction, that the reaction was actually already complete after 2 hours. Constant pressure was attained much earlier than in example 3, where the full 5 hours were needed for complete reaction, because portions of the catalytically active species decompose as a result of the high thermal stress at the high temperatures from example 3. These reaction conditions are also advantageous because some potential alcohols which are used in the alkoxylation decompose even in the event of lasting thermal stress at 160° C.

OHN: 267 mg KOH/g
Polydispersity (GPC): 1.125
Viscosity: 154 mPas
$p_{max,1}$=3.19 bar
$p_{max,2}$=2.75 bar
Metering time: 240 minutes
Metering rate: 0.62 g/min The analysis of the products obtained by this method has, as main products, the expected propoxylates based on glycerol and diethylene glycol. A characteristic by-product which is likewise found is the propoxylate of the catalyst.

An example here is the detection of the formal propoxylates of imidazolium by means of HPLC-MS coupling:

$[M]^+$ 271, 387, 445 amu

These masses indicate propoxylates (n=3, 5, 6) of the 1,3-dimethylimidazolium cation.

The invention claimed is:

1. A process for preparing a polyetherol by catalytic ring-opening polymerization of an alkylene oxide with a Zerevitinov-active compound Z1 and optionally a Zerevitinov-active compound Z2, the process comprising:
   initially charging a nitrogen-containing cyclic compound (A) of formula (I)

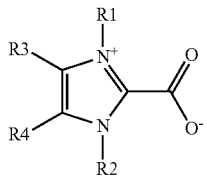

where R1 and R2 are each independently selected from alkyl and aryl, R3 and R4 are each independently selected from H, alkyl, aryl, or where R1 and R3, R3 and R4 or R2 and R4 form a ring, together with the Zerevitinov-active compound Z1 or a mixture thereof, and heating to a temperature of from 140° C. to 180° C., for a duration of 5 to 30 minutes; and
   conducting metered addition of the alkylene oxide, optionally in the presence of Z2,
wherein the temperature during the reaction with the alkylene oxide in the metered addition, after the charging and heating, is from 90° C. to 140° C.

2. The process according to claim 1, wherein R1 and R2 in formula (I) are each primary alkyl groups.

3. The process according to claim 1, wherein R1 in formula (I) is a primary alkyl group and R2 is a secondary alkyl group.

4. The process according to claim 1, wherein R1 and R2 in formula (I) are each secondary alkyl groups.

5. The process according to claim 1, wherein the metered addition is not conducted until after the end of the charging and heating.

6. The process according to claim 1, wherein the metered addition already commences during the duration of the charging and heating.

7. The process according to claim 1, wherein the alkylene oxide is at least one selected from the group consisting of ethylene oxide, propylene oxide, and butylene oxide.

8. The process according to claim 1, wherein the Zerevitinov-active compound Z1 is at least one selected from the group consisting of alcohols, sugar compounds, polyhydric phenols, resols, formaldehyde, and dialkanolamines.

9. The process according to claim 1, wherein the Zerevitinov-active compound Z1 is at least one selected from the group consisting of primary and secondary aliphatic and aromatic amines.

10. The process according to claim 1, wherein the Zerevitinov-active compound Z2 is at least one selected from the group consisting of alcohols, sugar compounds, polyhydric phenols, resols, formaldehyde, and dialkanolamines.

11. The process according to claim 1, wherein the Zerevitinov-active compound Z2 is at least one selected from the group consisting of primary and secondary aliphatic and aromatic amines.

12. The process according to claim 1, wherein at least two Zerevitinov-active compounds Z1 are employed, a Zerevitinov-active compound Z1a being at least one selected from the group consisting of alcohols, trimethylolpropane, pentaerythritol, sugar compounds, polyhydric phenols, resols, formaldehyde, and dialkanolamines, and a Zerevitinov-active compound Z1b being at least one selected from the group consisting of primary and secondary aliphatic and aromatic amines.

13. The process according to claim 1, wherein the Zerevitinov-active compound Z1 is the same as the Zerevitinov-active compound Z2.

14. The process according to claim 1, wherein the Zerevitinov-active compound Z1 is not the same compound as the Zerevitinov-active compound Z2.

15. The process according to claim 1, wherein a lactone compound is present in addition to the alkylene oxide in the metered addition.

16. A polyetherol obtained by the process of claim 1.

17. A process of preparing a polyurethane, comprising employing a polyetherol obtained by the process of claim 1.

* * * * *